(12) United States Patent
Evtodienko et al.

(10) Patent No.: US 6,444,169 B1
(45) Date of Patent: Sep. 3, 2002

(54) TEST-DEVICE FOR THRESHOLD GLUCOSE DETECTION IN URINE

(75) Inventors: Vladimir Evtodienko, Elkhart, IN (US); Iouri Evtodienko, Elkhart, IN (US); Lydia Dobler, Granger, IN (US); Michael A. Van Lente, Elkhart, IN (US); Ronald A. Lewis, II, St. Louis, MO (US)

(73) Assignees: Ralston Purina Company, St. Louis, MO (US); Environmental Test Systems, Inc., Elkhart, IN (US)

( * ) Notice: Subject to any disclaimer, the term of this patent is extended or adjusted under 35 U.S.C. 154(b) by 0 days.

(21) Appl. No.: 09/883,874

(22) Filed: Jun. 18, 2001

(51) Int. Cl.$^7$ ............................................... G01N 21/00
(52) U.S. Cl. ............................ 422/56; 422/61; 436/95; 436/169
(58) Field of Search ..................... 435/15, 10; 422/56, 422/57, 61, 68.1; 436/95, 169

(56) References Cited

U.S. PATENT DOCUMENTS

| | | | |
|---|---|---|---|
| 3,814,668 A | 6/1974 | Blake et al. | |
| 3,886,045 A | 5/1975 | Meiattini | |
| 3,964,817 A | 6/1976 | Humphrey | |
| 3,964,871 A | 6/1976 | Hochstrasser | |
| 4,303,753 A | 12/1981 | Lam | |
| 4,340,669 A | 7/1982 | Bauer | |
| 4,427,770 A | 1/1984 | Chen et al. | |
| 5,036,000 A | 7/1991 | Palmer et al. | |
| 5,183,742 A | 2/1993 | Omoto et al. | |
| 5,185,247 A | 2/1993 | Ismail et al. | |
| 5,217,691 A | 6/1993 | Greene et al. | |
| 5,418,142 A | * 5/1995 | Kiser et al. | 435/14 |
| 5,563,042 A | 10/1996 | Phillips et al. | |
| 5,620,863 A | * 4/1997 | Tomasco et al. | 435/14 |
| 5,824,491 A | 10/1998 | Priest et al. | |
| 6,162,397 A | * 12/2000 | Jurik et al. | 422/56 |

FOREIGN PATENT DOCUMENTS

| | | |
|---|---|---|
| EP | 0 060 133 B1 | 9/1982 |
| EP | 0 182 225 B1 | 8/1985 |

* cited by examiner

*Primary Examiner*—Jeffrey Snay
*Assistant Examiner*—Samuel Siefke
(74) *Attorney, Agent, or Firm*—Barnes & Thornburg

(57) ABSTRACT

Devices and test kits are provided for glucose detection and quantification in urine. The devices and kits comprise a chromogenic indicator mixture comprising a first indicator capable of color development to indicate the presence of a low-to-medium concentration of glucose, a second indicator capable of color development to indicate the presence of a higher concentration of glucose, wherein the first indicator prevents color development of the second indicator unless the higher concentration of glucose is present in the urine, and a non-chromogenic scavenger that interferes with color development of the first indicator when glucose levels are below a threshold concentration, and a carrier impregnated with the chromogenic indicator mixture.

21 Claims, No Drawings

TEST-DEVICE FOR THRESHOLD GLUCOSE DETECTION IN URINE

FIELD OF THE INVENTION

The present invention relates to a dry chemistry test device for glucose detection in liquid samples. More particularly, the invention is directed to a test device for threshold detection and quantification of glucose in urine and to methods of making and using the same.

BACKGROUND AND SUMMARY OF THE INVENTION

The detection of glucose levels is important in the treatment of diabetes. Test devices for glucose testing of the blood and urine of human diabetics, including many dry chemistry test devices or test strips, are described in numerous papers and patents. Glucose tests have been available in a dry test strip format for more than three decades. Analysis of blood and urine using test strips plays an important role in the diagnosis and treatment of human diabetes.

The history of dry chemistry disposable test-devices for glucose detection is summarized in U.S. Pat. Nos. 3,964,871 and 5,563,042. Quick and simple glucose determination in body fluids using dry chemistry test devices under field conditions is important for the early detection, diagnosis, and control of both human and animal diabetes. Key requirements for dry chemistry colorimetric tests are to detect glucose in a wide range of concentrations and to achieve easily discernable color distinctions at variously defined glucose levels.

For detection of relatively low glucose levels with test strips, several reagents have been proposed. U.S. Pat. No. 3,886,045 describes a non-toxic indicator comprising 4-aminoantipyrene and phenolic compounds that can form colored quinones in the presence of glucose. In U.S. Pat. No. 4,427,770, there is described a similar formulation using 4-aminoantipyrene, in a two pad test format to detect a wide range of glucose levels. U.S. Pat. No. 5,824,491 reports that 4-aminoantipyrene produces a gradual concentration/reflectance response from 0–400 mg/dL, with a linear concentration/reflectance response in the 150–400 mg/dL glucose range.

A sensitive and stable glucose test device was also described in U.S. Pat. No. 5,183,742. The test-device comprises a support having printed or coated detection reagent region on a surface. However, with only one peroxidatively active indicator, it proved difficult to obtain well discernable color changes over the broad range of 20–500 mg/dL.

Other indicator types have been used for detection and quantification of relatively high glucose levels and of a relatively wide range of glucose levels. In U.S. Pat. Nos. 4,303,753 and 4,340,669, an indicator in combination with a polymer (iodide +poly(vinylpyrrolidone)) is described for high range (500–1000 and 1000–10,000 mg/dL) glucose detection. Iodide salts have also been used in conjunction with a blue dye that fades in the presence of hydrogen peroxide. See, e.g., U.S. Pat. No. 3,814,668. The two components act in concert to provide a continuum of indicator colors.

A threshold color control system was described in U.S. Pat. No. 5,036,000. The system was designed for measurement of AND(P)H. Analytes react to form AND(P)H which is, in turn, oxidized by a chromogen. Non-chromogen competing compounds, such as Fe(III) compounds, are added to prevent a visible color change until a predetermined amount of AND(P)H is exceeded. When the predetermined amount of AND(P)H is exceeded, a single, easy to discern, color change is produced.

The above-mentioned reagents and test devices were generally designed for human urine testing. However, diabetes also afflicts animals. For example, feline diabetes is quite common, affecting about 0.2% to 1.0% of the cat population. In this affliction, glucose levels in the blood must be controlled. As with humans afflicted with diabetes, hyperglycemic cats are treated with insulin injections. While insulin treats the hyperglycemia, proper treatment of diabetes also requires periodic monitoring of glucose levels. Since elevated glucose levels in blood usually lead to elevated glucose levels in urine, periodic monitoring of glucose levels in the urine would provide needed screening for proper animal treatment.

While both the patent and non-patent literature is replete with reference to glucose testing systems and devices, few dry chemistry glucose tests have been developed specifically for testing the body fluids of animals. European Patent No. 0 060 133 describes a method and device for nonenzymatic glucose measurement in animal body fluids. Recently, a test strip product (Petstix™ 7, Bayer Agricultural Division (Etobicoke, Ontario, Canada)) for animal urine testing (including glucose test) was introduced in the market. Petstix 7 uses the same color blocks as N-Multistix™ SG (Bayer Diagnostics Division (Elkart, Ind.)), which is marked with U.S. Pat. No. 3,814,668.

There are several limitations and specific requirements for animal urine testing with test strips. For example, there are salient compositional differences between cat urine and human urine. One such difference is that cat urine has a significantly higher specific gravity than does human urine. Because of this difference, false readings may be obtained if test strips designed for human use are used for glucose detection in cats. Another limitation involves the problems in collecting a urine sample from the animal. In use with animal body fluids, it is also preferable to have a test device wherein the results are not dependent upon the amount of sample applied and the time of exposure to ambient conditions prior to activation, and wherein the results are stable for a prolonged period of time subsequent to activation.

SUMMARY OF THE INVENTION

The present invention is directed to a method, reagent composition, and dry chemistry test device for threshold glucose detection, particularly in cats. The device is in the form of an indicator impregnated substrate that is preferably cut into pieces suitable for being distributed onto cat litter. The indicator/substrate combination is selected so that after being wetted by animal urine, the indicator result remains discernable for a sufficient period of time to allow it to be observed by the pet owner or caretaker. Thus, the preferred indicator composition should not only be able to withstand the ambient conditions of a litter box and prolonged exposure to these conditions until activation by animal urine, but it should also have good stability even after activation with urine. The indicator reagent preferably should also be selected to indicate whether the reagent device has been contacted by animal urine, regardless of whether abnormal glucose levels are present.

The reagent composition used in the present invention is based on a standard glucose enzymatic system including glucose oxidase and peroxidase, and a combination of peroxidatively active indicators (chromogens). The combination of chromogens of the present invention provides for good color differentiation corresponding to a variety of urine glucose concentrations. Furthermore, glucose detection in cat urine is preferably based on an established sensitivity threshold or concentration threshold. At glucose concentrations less than the threshold, there would be no discernible color change on the test device. To achieve the desired sensitivity threshold, in addition to the combination of chromogens, the reagent composition includes a scavenger of peroxide/oxidized chromogens. The reagent composition undergoes a color change only when exposed to urine having a glucose concentration at or above the threshold level, and, when such occurs, easily visually discernible color changes indicate higher glucose concentrations.

In one preferred embodiment the test device is prepared using a cellulose paper substrate impregnated with a solution of the reagent composition. The paper is then dried and cut into small but visually detectable pieces to provide a device that may be distributed on cat litter. The inactivated device remains glucose sensitive for several days even at high humidity. After contact with cat urine, a color indicative of glucose concentration develops and persists for a period of time sufficient to allow the pet caretaker to observe the color development. Color stability is achieved by incorporating stabilizers and selected chromogens into the reagent composition.

Thus, one aspect of the invention includes a dry chemistry device for glucose detection and quantification in urine, said device comprising a chromogenic indicator mixture comprising a first indicator capable of color development to indicate the presence of a low-to-medium concentration of glucose, and a second indicator capable of color development to indicate the presence of a higher concentration of glucose, wherein the first indicator also prevents color development of the second indicator unless the higher concentration of glucose is present in the urine, and a carrier impregnated with the chromogenic indicator mixture.

In a preferred embodiment of this invention, a scavenger is provided to prevent color development when the glucose concentration is below a threshold concentration. Therefore, another aspect of the invention is a device for detection and quantification of glucose in urine comprising a chromogenic indicator mixture comprising a first chromogenic indicator reagent combination capable of color development to indicate the presence of a lower concentration of glucose and a second chromogenic indicator reagent combination capable of color development to indicate the presence of a higher concentration of glucose, wherein the first chromogenic indicator prevents color development of the second chromogenic indicator unless the higher concentration of glucose is present, a scavenger that prevents color development of the first indicator reagent composition unless a threshold concentration of glucose is present, and a matrix impregnated with the chromogenic indicator mixture.

A third aspect of this invention is a method for determining urine glucose concentration in an animal comprising the steps of selecting a test device comprising a matrix impregnated with a chromogenic indicator mixture comprising a first chromogenic indicator reagent combination capable of color development to indicate the presence of a lower concentration of glucose and a second indicator reagent combination capable of color development to indicate the presence of a higher concentration of glucose, wherein the first chromogenic indicator reagent combination prevents color development of the second indicator unless the higher concentration of glucose is present, locating the test device to promote incidental contact of same with animal urine, reading a developed indicator color after the device has been wetted with urine, and comparing the developed color to a standard color chart and determining the animal's urine glucose concentration.

Another aspect of this invention is a test kit for determining the concentration of glucose present in a sample of animal urine, the test kit comprising a substrate impregnated with a first chromogenic indicator reagent combination capable of color development to indicate the presence of a lower concentration of glucose, and a second chromogenic indicator reagent combination capable of color development to indicate the presence of a higher concentration of glucose, wherein the first chromogenic indicator prevents color development of the second chromogenic indicator unless the higher concentration of glucose is present in the urine sample; and a color chart indicating urine glucose concentrations corresponding to a plurality of discernible colors.

Additional features of the present invention will become apparent to those skilled in the art upon consideration of the following detailed description of preferred embodiments exemplifying the best mode of carrying out the invention as presently perceived.

DETAILED DESCRIPTION OF THE INVENTION

The present invention is directed to a method, reagent composition, and dry chemistry test device for glucose detection. While the invention is suitable for urine glucose detection generally, it is particularly suitable for urine glucose detection in cats. Preferably, the device is used for detection of glucose concentrations above a specific threshold level. In one preferred embodiment, the test device is formed as confetti-like material for use as a litter box additive. The problems presented by urine sample collection from cats and the relatively high specific gravity of cat urine present unique performance demands for the present test device relative to similar test strips used for testing of human diabetes.

The test device comprises an indicator mixture composition and a support matrix for the indicator composition. In a preferred embodiment, the support matrix comprises a piece of filter paper impregnated with the indicator composition, wherein the filter paper is of sufficient porosity and capillary affinity to allow an urinary sample from the animal to migrate into the matrix and interact with the indicator. The matrix may be a woven or a non-woven material and may include, but is not limited to, cellulosic natural fiber materials of the type normally used to make filter papers. Alternatively, organic polymer materials may be used. Other natural or synthetic fiber matrix materials, either woven or non-woven, may also be used.

It is preferable that the reagent indicator composition of the test device develop a threshold color response, wherein no discernible color change is produced unless the amount of glucose in the urine sample exceeds a predetermined Such would enable an animal owner or caretaker to observe the presence of a color change, indicating a possible hyperglycemic problem. Only if the threshold concentration were exceeded would the alerted caretaker need to investigate further to determine the severity of the hyperglycemic condition.

It is also preferable for the color differentiation to be strong enough to allow a reliable color detection and interpretation directly on the cat litter surface. Furthermore, the test device should remain glucose sensitive for at least several days, even at high humidity, after being applied on the cat litter surface. Additionally, the color signal of the urine activated device should be stable for at least several hours after exposure to cat urine. Other preferred features of the present test devices include that the color from the activated indicator reagent should not leach onto cat litter under conditions of normal use and observed test color should not depend on the amount of cat urine applied.

In one embodiment, the matrix impregnated with the indicator composition may be cut into small confetti-like pieces, to be sprinkled on or mixed into litter. The small pieces may be of various geometric shapes and typically .01 to 1.0 inches in its longest dimension, more typically, 0.1 to 0.5 inches in its longest dimension, and most typically squares or diamonds 0.2 inches on a side. However, it should be understood that the present invention is not limited for use with cats, and other shapes and sizes may be appropriate for human use or for use with other animals. For instance, much larger test sheets (1.0 to 20 inches in the longest dimension) may be suitable for use with paper-trained dogs. The larger sheets also may be placed under litter material in a cat litter box or under similar material for use with other animals. The test device may be sealed, for example in a foil package, to prolong product shelf life for distribution, sale, and use.

The reagents of the present invention are based on formulations having glucose oxidase, peroxidase, and chromogenic redox indicators as key components. Glucose is oxidized to gluconic acid by atmospheric oxygen in a specific glucose oxidase-catalyzed reaction that produces hydrogen peroxide as a byproduct proportional to the amount of glucose:

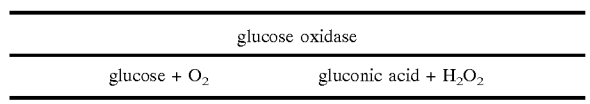

In various reactions catalyzed by peroxidase, hydrogen peroxide reacts with the colorless form of the indicator reagent composition to produce water and an oxidized, colored form of the indicator. The oxidized form of the indicator may itself be a colored entity or more typically reacts with another component to provide a colored product indicative of some concentration range of glucose in the tested sample. In the indicator mixture of the present invention two different indicator reagents are used; one to detect low/medium glucose levels (Ind 1) via Reaction 1, and another to provide a different colored signal at high glucose levels (Ind 2) via Reaction 2.

Reaction 1 uses an indicator reagent composition (Ind 1) that has a relatively rapid susceptibility to oxidation by peroxidase. Thus, Reaction 1 has a high reaction rate as compared to Reaction 2. In the presence of low/medium glucose levels (preferably 150–300 mg/dL), a component of Ind 1 is oxidized and corresponding colors (for example rose or red when Ind 1 is AAP/HBS) are developed. The device detects low/medium glucose levels mainly on the basis of Reaction 1:

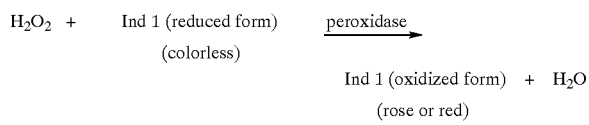

Suitable compositions for Ind 1 include 4-aminoantipyrene (AAP), or a salt thereof, and phenolic compounds, such as 2-hydroxy-3,5-dichlorobenzenesulfonate (HBS), 3-methylcatechol, 4-hydroxybenzenesulfonic acid, and 2,6-dimethylphenol. Other phenolic and aniline compounds capable of forming a colored compound with AAP are known in the art and are within the scope of this invention. See, for example, U.S. Pat. Nos. 3,886,045 and 4,427,770, hereby incorporated by reference. Other chromogenic aromatic compounds may be substituted for AAP. For example, 3-methylbenzothiazolinone hydrazone hydrochloride (MBTH) may be used. The combination of 1,3-phenylenediamine and MBTH produces an intense dull red color when activated with hydrogen peroxide.

In one embodiment of this invention, Ind 2 comprises an iodide salt. While potassium iodide is preferred, other iodide salts may be used, including but not limited to sodium iodide and ammonium iodide. The iodine that is released in Reaction 2 forms a colored complex with starch and other substances, as known in the art. See, for example, U.S. Pat. No. 3,886,045, hereby incorporated by reference. Substances capable of forming a colored complex with iodine include starch, starch components such as amylose or amylopectin, polyethylene glycol, polyvinylpyrrolidone, and polyvinyl alcohol. However, depending on the use, care must be taken in selecting a suitable substance, as some otherwise appropriate substances may be toxic. Because starch is relatively inexpensive, non-toxic, and provides good color, starch is preferred. Thus, Reaction 2 using iodide/starch is as follows:

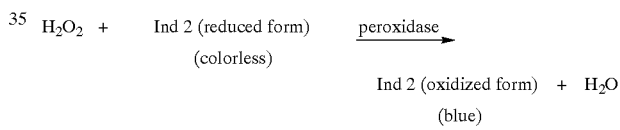

In the absence of any other indicator, iodide/starch produces a characteristic blue color in the 50–300 mg/dL range, with increasing blue color with increased glucose concentration.

Reaction 2 has been observed to proceed more slowly than Reaction 1. In a preferred embodiment, the total stoichiometric amount of Ind 1 in the reagent composition is equal to, or slightly exceeds, a low/medium glucose level. In the presence of low/medium glucose levels, Ind 1 quickly consumes the available peroxide and Reaction 2 does not proceed. When AAP/phenol is used, the only color change observed at lower concentrations is due to AAP/phenol. A similar scavenging effect is seen with MBTH/1,3-phenylenediamine. At high glucose levels (preferably above 300 mg/dL) all of Ind 1 is consumed and Ind 2 interacts with $H_2O_2$/peroxidase. As a result, a color specific for Ind 2 (for example dark brown-black or dark blue when Ind 2 is starch/iodate) is developed. Thus, Ind 2 is used mainly to detect high glucose levels.

In a preferred embodiment, in addition to the double indicator composition described above, a scavenger is used to provide a threshold detection level for the device, wherein no color change is observed at glucose urine levels below the threshold concentration. In this preferred embodiment, a scavenger is used to prevent a color change at very low levels of glucose, as shown in Reaction 3:

Reaction 3

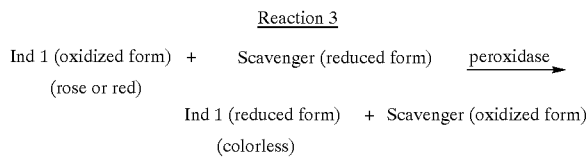

In the presence of very low glucose levels (preferably less than 50 mg/dL) the colored (oxidized) form of Ind 1 may be produced. However, a scavenger may be selected so that under conditions of low glucose concentration, the scavenger reacts with oxidized Ind 1 and transforms it back to the colorless reduced form. Thus, in these conditions no color is developed and only the background coloration can be seen. Alternatively, a scavenger may be used that out-competes the Ind 1 indicator for peroxide, preventing Reaction 1 from proceeding in low levels of glucose. In either case, predetermined amounts of the scavenger in the formulation correspond to a very low glucose level. In the presence of glucose levels greater than the capacity of the scavenger (preferably 50 mg/dL and more), the concentration of the oxidized Ind 1 exceeds the concentration of the scavenger, Ind 1 remains in its oxidized form, and glucose is detected. Depending on the application, suitable scavengers include stannous chloride, thiosulfates, and mercaptans. Because it is non-toxic, a preferred scavenger is cysteine.

Urine from diabetic cats undergoing insulin therapy should have some residual urine glucose. Therefore, it is preferred that the test device indicate a level of 50 mg/dL, in order to detect or prevent an overdose. This threshold level may be varied for different animal or human applications.

The above-described combination of indicators and scavengers provides a threshold glucose detection, as well as various indicator colors in the low-high urine glucose concentration range associated with diabetes in cats. It should be stressed that the threshold color change may be shifted as needed for individual applications, particularly in the 50–1000 mg/dL glucose range. Appropriate amounts of Ind 1 and scavenger may be chosen to produce a threshold color and an Ind 1/Ind 2 color change at desirable glucose levels.

It is preferred that the test device have good stability and be able to withstand ambient conditions of a litter box and prolonged exposure of these conditions until its activation by being wetted with animal urine. Also, it is preferred that the resultant color produced upon activation by the animal urine remain unchanged for a significant period of time. In this regard, the scavenger (for example, cysteine) included in the reagent formulation plays a dual role. The scavenger not only facilitates color distinction between very low and low glucose levels, but it also provides an antioxidant function to protect the indicators from spontaneous oxidation during reagent preparation, storage, and application.

In a preferred embodiment of the invention, the reagent composition is formulated to contain a polysaccharide, such as Dextran, DEAE-Dextran, or Alginate, to improve enzyme stability and to maintain adequate test performance of the test device during prolonged exposure to ambient conditions on cat litter. Furthermore, a film-forming polymer, such as poly(vinyl alcohol), may be used in the reagent composition to aid in preventing the indicator from leaching from the reagent when activated with cat urine.

The following examples are set forth to illustrate the principles and practices of the present invention to one skilled in the art. They are not intended to be restrictive but merely to be illustrative of the invention.

EXAMPLE 1

TABLE 1

Reagent Formulation No 1

| Components | Amount, g/L Distilled Water |
|---|---|
| Submix 1 for First Dip | |
| Starch | 6.0 |
| Submix 2 for Second Dip | |
| Glucose oxidase | 43 ku/L |
| Peroxidase | 36 ku/L |
| Potassium Iodide | 10.2 |
| 4-Aminoantipyrene | 1.86 |
| 2-Hydroxy-3,5-dichlorobenzenesulfonate Na-salt | 0.8 |
| Tartrazine (Acid Yellow) | 0.05 |
| L-Cysteine | 0.2 |
| Citric Acid | 2.3 |
| Citrate, Na-salt | 11.2 |
| Poly(vinyl alcohol) | 20.0 |
| Dextran | 10.0 |

Cellulose paper was impregnated with Submix 1 and dried. The resulting paper was impregnated with Submix 2 and dried again. The test paper impregnated with the entire set of the components was cut into small confetti-like pieces to obtain a final test device.

The test device pieces were distributed on the surface of cat litter and samples of 60 microliters of cat urine having different glucose concentrations were applied to the pieces. The color developed was analyzed visually and instrumentally by reflectance spectrophotometry.

TABLE 2

Visual and instrumental color evaluations.

| Glucose Levels mg/dL | Test Piece Colors | Color Difference vs. Non-Activated Test Piece |
|---|---|---|
| Not activated (not wetted by cat urine) | Yellow | — |
| Activated with 50 mg/dL or less | Light Tan | 9.37 (50 mg/dL) |
| 150 | Rose | 19.78 |
| 300 | Red | 42.13 |
| 600 | Dark brown-black | 56.30 |

Urine with a specific gravity of 1.030 was used and observed one hour after activation. The color differences are given in CIELAB delta E Units and are based on instrumental reflectance measurement. The color difference units represent the relative distinction by a normal observer of the color at the indicated concentration compared to the yellow (not activated) color.

EXAMPLE 2

TABLE 3

Reagent Formulation No. 2

| Components | Amount, g/L or activity units |
|---|---|
| Glucose oxidase | 104.3 kilounits |
| Peroxidase | 56.9 kilounits |
| Potassium Iodide | 9.92 |
| Starch | 6.40 |
| 4-Aminoantipyrene | 2.42 |

TABLE 3-continued

Reagent Formulation No. 2

| Components | Amount, g/L or activity units |
|---|---|
| 3-Methylcatechol | 1.48 |
| L-Cysteine | 1.7 |
| Citric Acid | 38.4 |
| Imidazole | 1.0 |
| Alginic Acid | 5.0 |
| Triton X-1000 | 2.5 |

Filter paper was dipped into this solution and dried. The paper was then cut into pieces. For Reagent Formulation No. 2, the color chart is as follows:

| Glucose Conc. (mg/dL) | Test Piece Color |
|---|---|
| 50 | light yellow |
| 150 | very light olive |
| 300 | olive drab |
| 600 | brown |

The resultant test device was tested with cat urine containing glucose concentration levels of 50, 150, 300 and 600 mg/dL. Prior to application on the test device, the specific gravity of each of the cat urine samples was adjusted with water to either 1.020 of 1.050. With the lower specific gravity urine samples, colors developed within a few minutes, with the color corresponding to the glucose level in the sample. The rate of color development with the higher specific gravity urine samples was slower than that of the lower specific gravity samples. However, after ten minutes, the colors of the higher specific gravity series appeared similar to the lower specific gravity series. Thus, with higher specific gravity the rate of color development was slowed, but the resultant color was sufficiently distinct to identify the various glucose levels.

EXAMPLE 3

Stability of the Reagent after Activation with Cat Urine

Using Reagent Formulation No. 1 according to Example 1, test readings were done at various times after activation with cat urine (specific gravity 1.030). The resulting color was read visually and the glucose concentration was determined by color comparison with a predetermined color chart. As shown in Table 4, the test readings are stable for at least 8 hours after activation with cat urine.

TABLE 4

| Hours after reagent activation with cat urine | Actual glucose urine level, mg/dL | | | |
|---|---|---|---|---|
| | 0 | 150 | 300 | 600 |
| | Measured glucose urine level, mg/dL | | | |
| 1 | 0 | 155 | 320 | 600 |
| 4 | 0 | 157 | 310 | 600 |
| 8 | 0 | 150 | 310 | 600 |

Effect of Cat Urine Specific Gravity

Using Reagent Formulation No. 1 according to Example 1, test readings were done four hours after activation with cat urine having varying specific gravities. The resulting color was read visually and the glucose amount was evaluated by color comparison with a predetermined color chart. As shown in Table 5, specific gravity has only minimal effect on the results.

TABLE 5

| Specific Gravity | Actual glucose urine level, mg/dL | | |
|---|---|---|---|
| | 150 | 300 | 600 |
| | Measured glucose urine level, mg/dL | | |
| 1.020 | 160 | 310 | 600 |
| 1.040 | 135 | 290 | 585 |
| 1.050 | 127 | 275 | 555 |

Effect of the Quantity of Urine Applied

Using Reagent Formulation No. 1 according to Example 1, test readings were done one hour after activation with varying amounts of cat urine (specific gravity of 1.030). The resulting color was read visually and the glucose concentration was determined by color comparison with a predetermined color chart. As shown in Table 6, the amount of urine applied in the range of 60–150 microliters does not significantly affect test readings. Also, it was noted that larger volumes of urine do not seem to cause significant leaching of indicators from test pieces.

TABLE 6

| Microliters applied to the test-piece of 1 cm² | Actual glucose urine level, mg/dL | | |
|---|---|---|---|
| | 150 | 300 | 600 |
| | Measured glucose urine level, mg/dL | | |
| 30 | 112 | 250 | 525 |
| 60 | 150 | 300 | 600 |
| 90 | 150 | 300 | 600 |
| 120 | 150 | 320 | 600 |
| 150 | 150 | 320 | 600 |

Although the invention has been described in detail with reference to preferred embodiments, variations and modifications exist within the scope and spirit of the invention as described and defined in the following claims.

What is claimed is:

1. A dry chemistry device for glucose detection and quantification in urine, said device comprising
    a chromogenic indicator mixture comprising
        a first indicator capable of color development to indicate the presence of a low-to-medium concentration of glucose, and
        a second indicator capable of color development to indicate the presence of a higher concentration of glucose, wherein the first indicator prevents color development of the second indicator unless the higher concentration of glucose is present in the urine, wherein the chromogenic indicator mixture further comprises a non-chromogenic scavenger that interferes with color development of the first indicator when glucose levels are below a threshold concentration of glucose; and a carrier impregnated with the chromogenic indicator mixture.

2. The device of claim 1 wherein the non-chromogenic scavenger comprises cysteine.

3. The device of claim 1 wherein the non-chronogenic scavenger is selected from the group consisting of thiosulfates and mercaptans.

4. The device of claim 1 wherein the threshold glucose concentration is about 50 mg/dL.

5. The device of claim 4 wherein the low-to-medium concentration of glucose is in the range of 150–300 mg/dL.

6. The device of claim 5 wherein the higher concentration of glucose is 300 mg/dL and the second indicator is capable of color development to indicate concentrations of glucose in the range of 300–600 mg/dL.

7. The device of claim 1 wherein the first indicator comprises 4-aminoantipyrene and a phenolic compound.

8. The device of claim 7 wherein the phenolic compound is selected from the group consisting of 2-hydroxy-3,5-dichlorobenzenesulfonate, 3-methylcatechol, 4-hydroxybenzenesulfonic acid, and 2,6-dimethylphenol.

9. The device of claim 1 wherein the second indicator comprises an iodide salt.

10. The device of claim 9 wherein the iodide salt is potassium iodide and the second indicator further comprises starch.

11. The device of claim 1 wherein the chromogenic indicator mixture further comprises a stabilizer that prevents loss of capacity for color development for at least 24 hours at high humidity.

12. The device of claim 1 wherein the color development remains stable for at least eight hours subsequent to activation.

13. The device of claim 1 wherein the carrier is cellulose paper.

14. The device of claim 13 wherein the cellulose paper is formed into small but visually detectable pieces.

15. The device of claim 1 wherein a resultant color obtained from the color development is independent of the specific gravity of the urine.

16. A device for detection and quantification of glucose in urine comprising:

a chromogenic indicator mixture comprising
a first chromogenic indicator reagent combination capable of color development to indicate the presence of a lower concentration of glucose, and
a second chromogenic indicator reagent combination capable of color development to indicate the presence of a higher concentration of glucose, wherein the first chromogenic indicator prevents color development of the second chromogenic indicator unless the higher concentration of glucose is present,
a scavenger that prevents color development of the first indicator reagent composition unless a threshold concentration of glucose is present, and
a matrix impregnated with the chromogenic indicator mixture.

17. The device of claim 16 wherein said matrix formed into small but visually detectable pieces suitable for application in a litter box.

18. A test kit for determining the concentration of glucose present in a sample of animal urine comprising a substrate impregnated with a chromogenic indicator mixture comprising
a first indicator capable of color development to indicate the presence of a lower concentration of glucose, and
a second indicator capable of color development to indicate the presence of a higher concentration of glucose, wherein the first indicator prevents color development of the second indicator unless the higher concentration of glucose is present in the urine sample; wherein the substrate is further impregnated with a scavenger that prevents color development of the first indicator unless a threshold concentration of glucose is present in the urine; and
a color chart indicating urine glucose concentrations corresponding to a plurality of discernible colors.

19. The test kit of claim 18 wherein the color chart provides colors corresponding to urine glucose concentrations of 0, 50, 150, 300, and 600 mg/dL.

20. The test kit of claim 18 wherein the substrate is formed into small but visually detectable pieces.

21. The test kit of claim 18 wherein the substrate is provided in a sealed foil package.

* * * * *

UNITED STATES PATENT AND TRADEMARK OFFICE
CERTIFICATE OF CORRECTION

PATENT NO.    : 6,444,169 B1
DATED         : September 3, 2002
INVENTOR(S)   : Evtodienko et al.

It is certified that error appears in the above-identified patent and that said Letters Patent is hereby corrected as shown below:

<u>Column 10,</u>
Line 59, should read -- 3. The device of claim 1 wherein the non-chromogenic scavenger is selected from the group consisting of thiosulfates and mercaptans. --

Signed and Sealed this

Fourth Day of February, 2003

JAMES E. ROGAN
*Director of the United States Patent and Trademark Office*